US00PP12165P2

(12) United States Plant Patent
Lyrene

(10) Patent No.: US PP12,165 P2
(45) Date of Patent: Oct. 23, 2001

(54) BLUEBERRY PLANT CALLED 'EMERALD'

(76) Inventor: Paul M. Lyrene, University of FL, P.O. Box 110690, Gainesville, FL (US) 32611-0690

( * ) Notice: Subject to any disclaimer, the term of this patent is extended or adjusted under 35 U.S.C. 154(b) by 0 days.

(21) Appl. No.: 09/392,389

(22) Filed: Sep. 9, 1999

(51) Int. Cl.[7] ..... A01H 5/00
(52) U.S. Cl. ..... Plt./157
(58) Field of Search ..... Plt./157

*Primary Examiner*—Bruce R. Campell
*Assistant Examiner*—June Hwu

(57) ABSTRACT

A new and distinct low-chill, tetraploid highbush blueberry (Vaccinium) variety of complex ancestry, based largely on *V. corymbosum* L. with some genes from *V. darrowi* Camp. Its *V. darrowi* genes derive from the fact that the recurrent selection program that gave rise to 'Emerald', while largely based on *V. corymbosum* parentage, also involved some *V. darrowi* clones. Because 'Emerald' is of interspecific origin, it does not correspond to any botanical species, but rather, combines genes from the two species *V. corymbosum* and *V. darrowi*. The novelty of the new clone consists of the following unique combination of features:

1. Produces a vigorous, upright plant with high yield potential.

2. Flowers and produces new spring vegetation vigorously in Florida in areas where the mean January temperature is 62° F. or colder.

3. Produces fruit that are large, firm, have a good picking scar, and a good flavor.

4. Can readily be propagated by softwood cuttings under mist.

5. Ripens 80% of its fruit between April 15 and May 10 in north-central Florida.

6. Ripens its fruit 60 days after flowering in north-central Florida.

7. Has moderate to high resistance to phytophthora root rot, botryosphaeria stem blight, botryosphaeria cane canker, and the leaf diseases that are common on blueberries in Florida.

3 Drawing Sheets

ORIGIN OF THE VARIETY

'Emerald' originated as a seedling from the cross, FL91-69 (unpatented)×NC1528 (unpatented), made in a greenhouse at the University of Florida in Gainesville in March 1991. FL91-69 was a seedling selected from the Florida blueberry-breeding program. It was never named or released as a cultivar because it did not have the combination of plant and berry characteristics needed for commercial blueberry production. In particular, its berries were smaller, darker, and softer than those of 'Emerald'. NC 1528 was a blueberry selection from the North Carolina State University blueberry-breeding program at Castle Hayne, N.C. Unlike 'Emerald', NC 1528 had a high chilling requirement and could not be grown successfully in Florida. It was never named or released as a cultivar. The seedling that gave rise to 'Emerald' was transplanted along with 10,000 other hybrid seedlings into a high-density field evaluation nursery in Gainesville in May 1992. In May 1993 the plant fruited for the first time and was among 500 seedlings saved for further evaluation. Based on its growth and fruiting performance in the field in the springs of 1994 and 1995 it was selected for propagation in May 1995. Ten plants were propagated from softwood cuttings and planted along with 100 other clones in field evaluation plots in Windsor, Fla. (latitude 29.7 north, longitude 82.2 west, elevation 100 feet). The original seedling was evaluated for 4 fruiting seasons in Gainesville, and the propagated plot was examined during the fruiting seasons of 1997, 1998, and 1999. One thousand plants were propagated by cuttings in the summer of 1998 and were transplanted to a test field at Archer in north-central Florida in December 1998.

ASEXUAL PROPAGATION OF THE VARIETY

More than 1000 plants of the variety have been propagated by softwood cuttings, and the resulting plants have manifested the varietal characteristics without exception.

SUMMARY OF THE VARIETY

'Emerald' appears to combine the high bush vigor, low chilling requirement, early ripening season, high yield potential, and high berry quality that is necessary for a successful commercial blueberry variety in north and central Florida. 'Emerald' is tetraploid with 2N=4X=48 somatic chromosomes. 'Emerald' plants have been hand pollinated and used as a pollen source for hand pollination of numerous other tetraploid southern highbush blueberry selections and varieties and has been highly fertile in all crosses. Although 'Emerald' is more self-compatible than most other Florida southern highbush blueberry varieties and produces a considerable amount of fruit when self pollinated, the variety produces more fruit, ripens earlier, and has larger berries if cross pollinated with another southern highbush variety. 'Emerald' breaks both vegetative and flower buds early in the spring even after unusually mild winters in Gainsville, Fla. Although there is increasing risk of fruit loss to spring freezes as the variety is planted in colder areas, 'Emerald' could probably be grown commercially in areas as cold as southeast Georgia and along the Gulf Coast to southeast Texas with occasional crop losses due to freezes. The ripening season of 'Emerald' in north and central Florida, late April and early May, is normally a period of low rainfall and low humidity in the southeastern United States, which facilitates harvest, and is also a period when fresh blueberry supplies are at a minimum and prices are highest. 'Emerald' has the following unique combination of features:

1. Produces a vigorous, upright plant with high yield potential.

2. Flowers and produces new spring vegetation vigorously in Florida in areas where the mean January temperature is 62° F. or colder.

3. Produces fruit that are large, firm, have a good picking scar, and a good flavor.

4. Can readily be propagated by softwood cuttings under mist.

5. Ripens 80% of its fruit between April 15 and May 10 in north-central Florida.

6. Ripens its fruit 60 days after flowering in north-central Florida.

7. Has moderate to high resistance to phytophthora root rot, botryosphaeria stem blight, botryosphaeria cane canker, and the leaf diseases that are common on blueberries in Florida.

BRIEF DESCRIPTION OF THE DRAWINGS

FIG. 1 illustrates the flowers of Emerald including their shape, approximate color, and arrangement in the clusters. Colors in the drawings are only approximate; in cases where the colors in the drawings differ from the Panetone color designations given in the paragraphs below, the Pantone designations should be considered the more accurate.

FIG. 2 illustrates in side view the leaves and fruit of Emerald, including the shape and color of the berries and their arrangement on the peduncle.

FIG. 3 illustrates in side view a 2.5-year old plant of Emerald in late April in a field in Gainesville, Fla. The plant is about 1.5 m tall.

DESCRIPTION OF THE VARIETY

The following is a detailed botanical description of the new and distinct variety of blueberry, its flowers, fruit and foliage, based on observations of specimens grown at Gainesville, Fla. and Windsor, Fla. Color descriptions, except those given in common terms, use terminology from "The Pantone Book of Color", 1990, by Leatrice Eiseman and Lawrence Herbert; Harry N. Abrams, Inc. Publishers, New York. In cases where the color descriptions cited from the Pantone Book of Color differ from the colors shown in the drawings, the colors cited from the Pantone Book of Colors should be considered accurate. Any deviations from these colors in the drawings is due to failure of the photographic process to exactly duplicate the colors of nature.

Bush: The following measurements were from plants 2.4 years after transplanting 1-year old rooted cuttings to the field.

*Height of plants.*—1.5 m.

*Canopy diameter.*—1.1 m.

*Plant vigor.*—Exceeds 'Sharpblue' (unpatented), 'Santa Fe' (U.S. Plant Pat. No. 10,788), 'Blue Crisp' (U.S. Plant Pat. No. 11,033), 'Sapphire' (U.S. Plant patent application Ser. No. 09/175,102), 'Jewel' (U.S. Plant Pat. No. 11,807), 'Star' (U.S. Plant Pat. No. 10,675), and 'Southmoon' (U.S. Plant Pat. No. 9,834).

*Growth habit.*—Upright to semi-spreading.

*Flower bud density (number per dormant branch).*—Medium to high.

Trunk:

*Suckering tendency.*—5 to 8 major stems from the base: moderately prolific in suckering.

*Texture of wood surface.*—New wood (less than one-year old): smooth; one-year-old wood: surface rough; three-year-old and older wood: surface becomes smooth by exfoliation of strips of bark.

*Color of 1-year old rough bark.*—"Champagne Beige" (Pantone 14-1012).

Twigs:

*Color of previous-year's smooth shoots on Apr. 12.*—"Honeygold" (Pantone 15-1142).

*Internode length.*—2.0 cm on strong spring shoots.

Leaves:

*Leaf arrangement.*—Alternate.

*Leaf venation.*—Pinnate.

*Leaf length.*—6.0 cm.

*Leaf width.*—3.5 cm.

*Leaf shape.*—Obovate with and acute base and mucronate apex; leaf apex terminates in a round gland, 0.3 mm diameter, conspicuous under 30 X magnification.

*Leaf margin.*—Entire except for a few marginal invaginations with round invaginate glands along the lateral margins of the leaves. These invaginations and glands are visible under 30X magnification with a stereoscopic microscope.

*Color of upper surface of leaves.*—"Black Forest" (Pantone 19-0315).

*Color of lower surface of leaves.*—"Water Cress" (Pantone 17-0220).

*Pubescence on upper leaf surface.*—Dense population of curly, white hairs on midrib. These hairs are visible under 30X magnification with a stereoscopic microscope.

*Pubescence on lower leaf surface.*—None.

*Pubescence on leaf margins.*—None. Several round glands on invaginations of margin on each side of blade. These are visible under 30X magnification with a stereoscopic microscope.

*Leaf arrangement and venation.*—Typical for *V. corymbosum.*

*Relative time of leafing vs. flowering.*—On Feb. 19, 1999: 80% of flowers were open with strong new leafing.

Flowers:

*Flower arrangement.*—Flowers arranged alternately along a short, leafless, deciduous branch.

*Pedicel length at the time of flower anthesis.*—6 mm.

*Peduncle length at time of anthesis.*—6 mm.

*Petals.*—Fused into a corolla tube with 5 lobes.

*Pollen color.*—"Ice" (Pantone 11-4803).

*Pollen staining with acetocarmine dye.*—95%.

*Pollen production per flower.*—Very abundant.

*Flower type.*—Perfect, ovary inferior, petals fused into a corolla tube, the 10 stamens inserted at the base of the corolla tube.

*Flower corolla shape.*—Cylindrical.

*Corolla texture.*—Smooth.

*Flower length from pedicel attachment point to corolla tip.*—11 mm.

*Length of corolla tube.*—9 mm.

*Length of the style plus stigma axis at anthesis from the top of the ovary to the tip of the stigma.*—9 mm.

*Color of fresh anthers in flower at anthesis.*—"Hazel" (Pantone 17-1143).

*Length of corolla tube.*—9 mm.

*Diameter of corolla tube at widest point.*—9 mm.

*Corolla aperture diameter.*—4 mm.

*Corolla color at anthesis.*—"Snow White" (Pantone 11-0602).

*Pedicel and peduncle color.*—"Peppermint" (Pantone 16-6329).

*Calyx color at anthesis.*—"Peppermint" (Pantone 16-6329).

*Longest calyx diameter at anthesis, measured from the tip of one calyx lobe to the tip of the opposite calyx lobe.*—8 mm.

*Number of calyx lobes.*—Five.

*Calyx surface.*—Smooth.

*Flower fragrance.*—Light honeysuckle fragrance.

*Flowering period.*—50% anthesis about February 15 in Gainseville.

*Flower cluster.*—(Tight, medium, or open): medium.

*Number of flowers per cluster.*—4 to 11, mostly about 6.

*Self-fruitfulness.*—Medium. Self-pollinated fruit yield about half as great as cross-pollinated yield.

Berry:

*Diameter of calyx aperture on mature berry.*—6–7 mm.

*Calyx lobes.*—The five calyx lobes not well developed on the mature berry, lobes small and inconspicuous.

*Berry cluster* (*tight, medium, or open*).—Medium.

*Pedicel length at berry maturity.*—7–8 mm.

*Peduncle length at berry maturity.*—6 mm.

*Number of berries per cluster.*—Normally 3–5.

*Berry weight.*—2.9 g for first ripe berries on leafy plants with a medium heavy crop.

*Berry height.*—13 mm.

*Berry width.*—18 mm.

*Berry color* (*ripe on plant*).—"Gull" (Pantone 17-3802).

*Berry color* (*after harvest and moderate handling*).—"Charcoal Gray" (Pantone 18-0601).

*Berry surface wax.*—Medium thick: medium to high durability when berry is handled.

*Berry skin color after polishing.*—"Shale" (Pantone 19-3903).

*Seed size.*—Well-developed seeds average 1.8 mm long×1.0 mm wide.

*Color of mature seeds after drying.*—"Rawhide" (Pantone 18-1137).

*Seed coat.*—Heavily lignified with numerous simple pits.

*Internal flesh color of mature berry.*—"Green Tint" (Pantone 13-6106).

*Pedicel scar.*—Small and dry.

*Berry firmness.*—High firmness.

*Berry flavor.*—Medium to good: sweet with some acidity.

*Berry texture.*—Thin skin, seeds not gritty.

*Maturity date.*—50% ripe May 1 in Gainesville. First commercial harvest (10% of the fruit ripe) typically April 22 at Gainesville. Last commercial harvest typically May 25 in Gainesville.

*Productivity.*—Yields up to 2,000 berries or 8 pounds per plant per year after $5^{th}$ year.

*Comparison with similar varieties.*—'Emerald' is most similar to 'Sharpblue' (unpatented) and 'Bluecrisp' (U.S. Plant Pat. No. 11,033). It differs most notably from 'Sharpblue' in having larger berries, firmer berries, a better picking scar (less tearing of the skin when the berry is separated from the pedicel), and more concentrated ripening season. It differs most notably from 'Bluecrisp' in earlier flowering, earlier ripening, larger berries, and in the production of more flower buds per stem, which results in greater numbers of flowers and berries and higher yields.

Resistance to diseases, insects, and mites:

*Phytophthora root rot.*—Resistance above average for southern highbush.

*Stem blight.*—Resistance average for southern highbush.

*Leaf spots.*—Resistance above average for southern highbush.

*Bud mites.*—Resistance above average for southern highbush.

Ease of propagation: Propagates readily from softwood cuttings under mist.

I claim:

1. A new and distinct highbush blueberry plant, substantially as illustrated and described, characterized by its low chilling requirement, early flowering, early ripening, high yield potential, large, sweet to sub acid berry, high berry firmness, small, dry picking scar, and medium to high resistance to the major blueberry pests in north Florida.

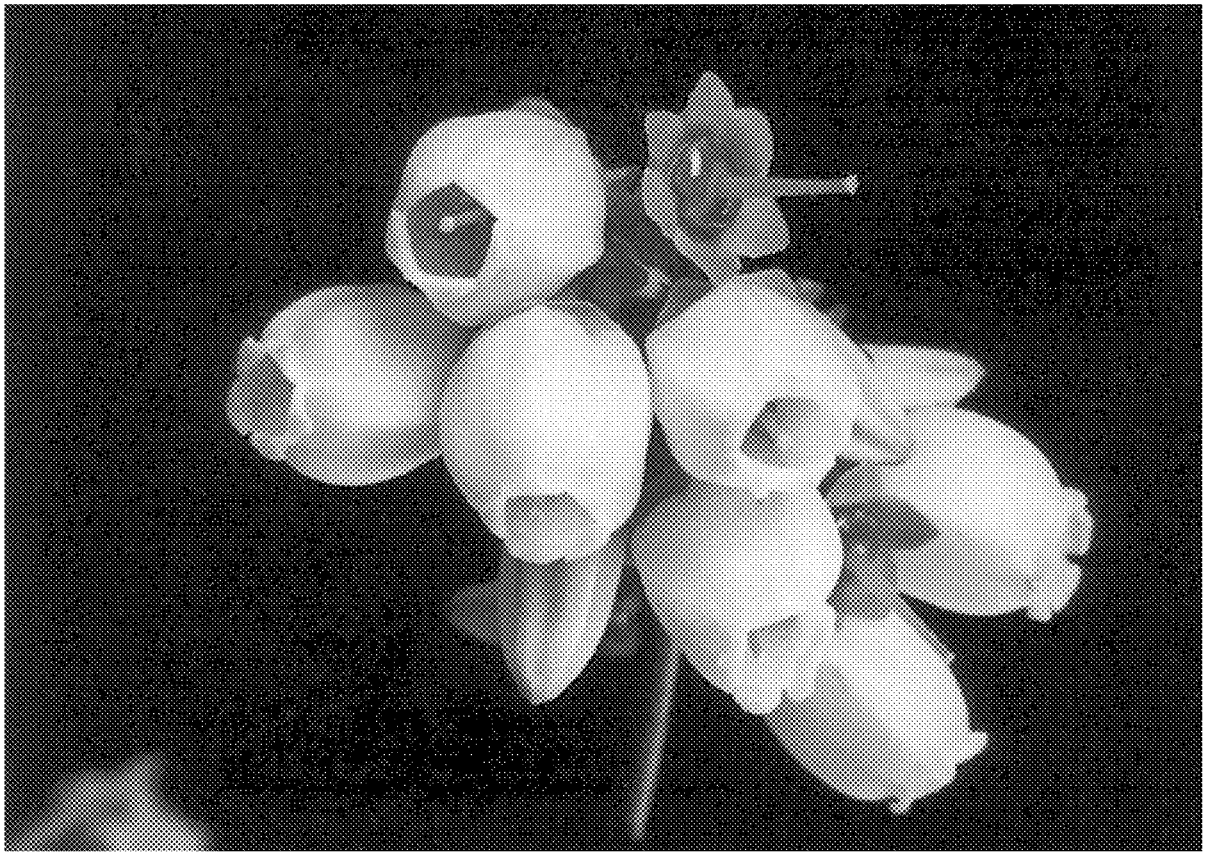

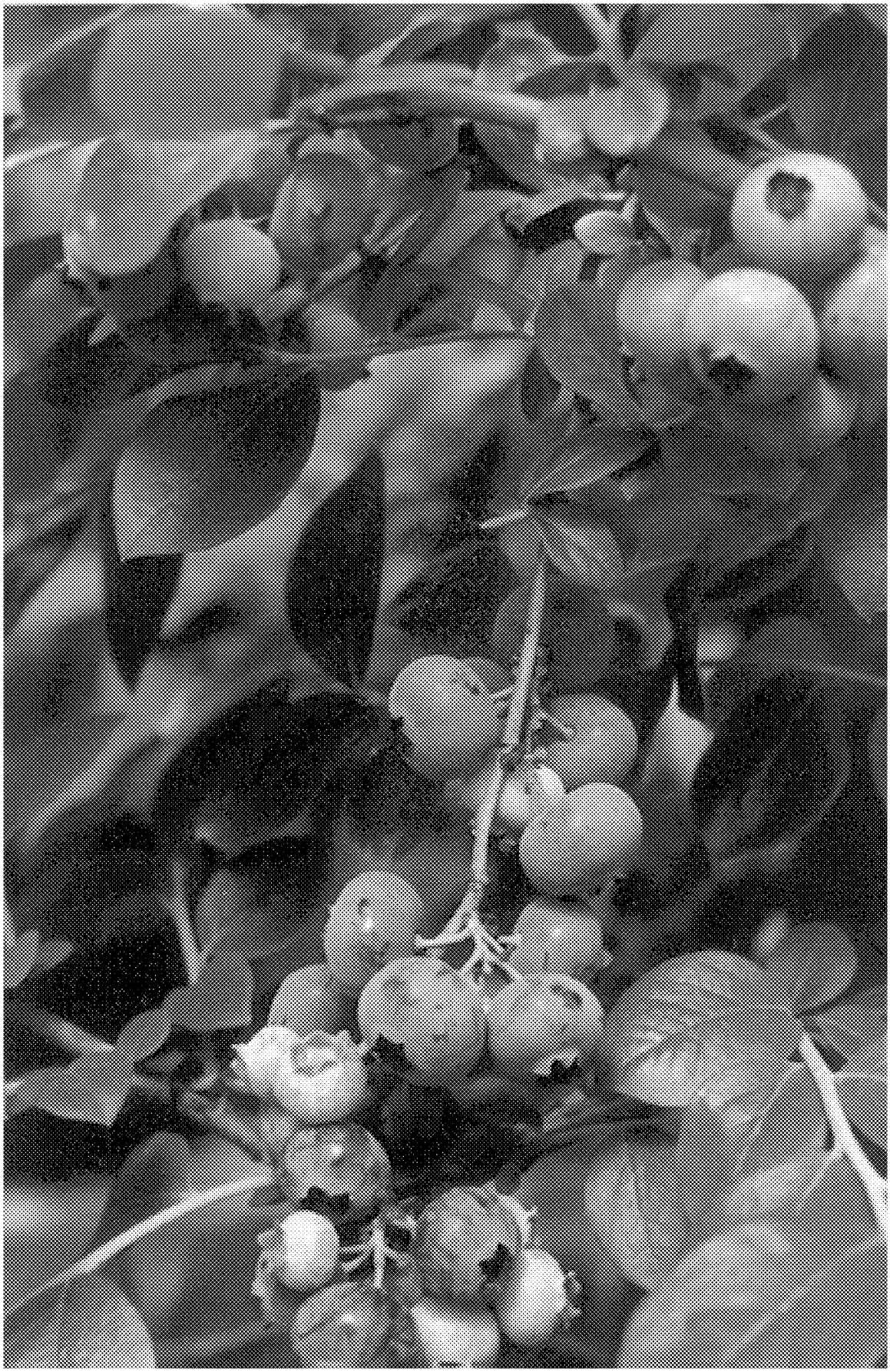

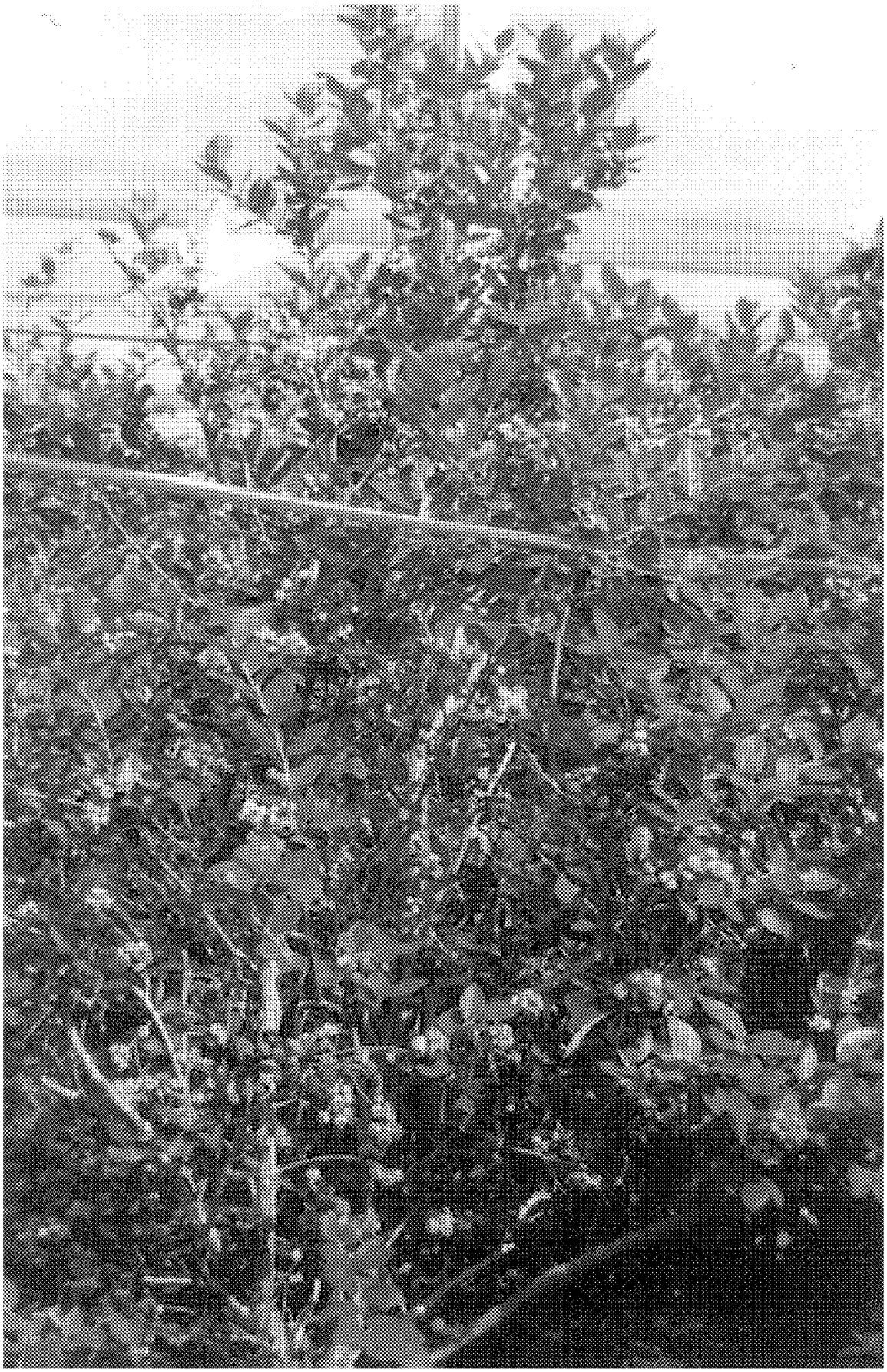

* * * * *